_United States Patent_ [19]

Weber et al.

[11] 3,984,416
[45] Oct. 5, 1976

[54] SUBSTITUTED QUINOLINE-8-CARBOXAMIDO ETHYL BENZENE-SULFONYL N-CYCLOPENTYLMETHYL UREA

[75] Inventors: Helmut Weber, Frankfurt am Main; Walter Aumüller, Kelkheim, Taunus; Rudi Weyer, Frankfurt am Main; Karl Muth, Kelkheim, Taunus; Volker Hitzel, Lorsbach, Taunus, all of Germany

[73] Assignee: Hoechst Aktiengesellschaft, Frankfurt am Main, Germany

[22] Filed: May 29, 1975

[21] Appl. No.: 581,764

Related U.S. Application Data

[62] Division of Ser. No. 308,002, Nov. 20, 1972, Pat. No. 3,927,088.

[30] Foreign Application Priority Data

Nov. 20, 1971  Germany............................ 2157607

[52] U.S. Cl............................................ 260/287 F
[51] Int. Cl.². .................................... C07D 215/18
[58] Field of Search................................ 260/287 F

[56] References Cited
UNITED STATES PATENTS 3,751,418  8/1973  Weyer et al.............. 260/287 F
3,816,424  6/1974  Weyer et al.............. 260/287 F _Primary Examiner_—Nicholas S. Rizzo
_Assistant Examiner_—David E. Wheeler
_Attorney, Agent, or Firm_—Curtis, Morris & Safford

[57] ABSTRACT

Sulfonyl-ureas of the formula X—CO—NH—A—SO$_2$—NH—CO—NH—R$^1$, in which R$^1$ represents cyclopentylmethyl, alkyl-cyclopentylmethyl or dialkyl-cyclopentylmethyl, having up to 2 carbon atoms in the alkyl rest, or cyclopentylethyl, X represents a.

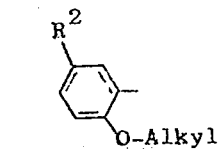

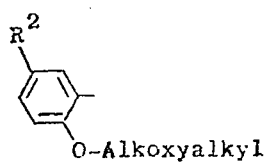

or 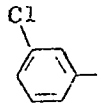

in which R$^2$ represents hydrogen, F, Cl, Br, CF$_3$, CH$_3$ or OCH$_3$, b.

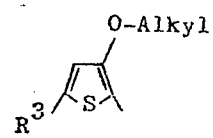

in which R$^3$ represents hydrogen, Cl or CH$_3$, c.

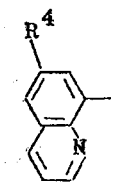

in which R$^4$ represents hydrogen, Cl or Br,

A represents one of the groupings

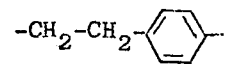

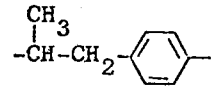

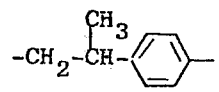

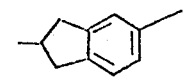

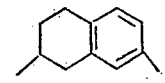

and their physiologically tolerated salts, process for preparing them and pharmaceutical preparations containing them.

2 Claims, No Drawings

SUBSTITUTED QUINOLINE-8-CARBOXAMIDO ETHYL BENZENE-SULFONYL N-CYCLOPENTYLMETHYL UREA

This is a divisional application of Application Ser. No. 308,002, filed Nov. 20, 1972, now U.S. Pat. No. 3,927,088, issued Dec. 16, 1975.

The present invention provides sulfonyl-ureas of the formula $$X-CO-NH-A-SO_2-NH-CO-NH-R^1$$

which, as substance or in the form of their salts, have blood sugar lowering properties and are distinguished by a strong and long lasting lowering of the blood sugar level.

In the above formula $R^1$ represents cyclopentylmethyl, alkyl-cyclopentylmethyl or dialkyl-cyclopentylmethyl, having up to 2 carbon atoms in the alkyl rest, or cyclopentylethyl, X represents a.

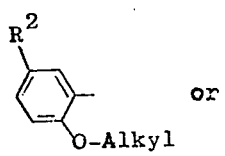

in which $R^2$ represents hydrogen, F, Cl, Br, $CF_3$, $CH_3$ or $OCH_3$, b.

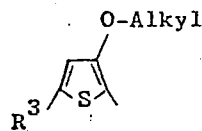

in which $R^3$ represents hydrogen, Cl or $CH_3$, c.

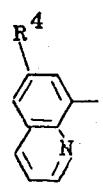

in which $R^4$ represents hydrogen, Cl or Br,

A represents one of the groupings

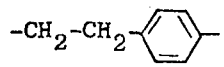

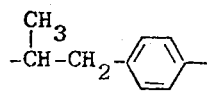

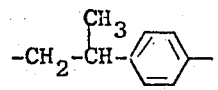

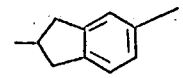

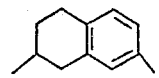

In the above and in the following definitions, "alkyl" stands for an alkyl group having 1 to 4 carbon atoms in a straight or branched chain, if not expressely stated otherwise.

The present invention furthermore provides a process for preparing these sulfonyl ureas, wherein a rest of the formula II $$X-CO-$$      II and a rest of the formula III $$-CO-NHR^1$$      III is introduced, optionally stepwise, into compounds having the group of the formula $$-HN-A-S(O)_n-$$      I in which $n$ stands for 0, 1 or 2, and wherein I and III are bound over a —NH— group which is contained in I or III, and, if necessary, the reaction products are oxidized and, if desired, treated with alkaline agents for salt formation.

The above-mentioned groups can be introduced, for example, a. by reacting an amine of the formula $R^1$-$NH_2$ or a salt thereof with a X-CO-NH-A-substituted sulfonyl-isocyanate, sulfonyl-carbamic acid ester, sulfonyl-thiolcarbamic acid ester, sulfonyl-urea, sulfonyl-semicarbazide or sulfonyl-semicarbazone, or a sulfonamide of the formula $$X-CO-NH-A-SO_2-NH_2$$

or a salt thereof with a $R^1$-substituted isocyanate, carbamic acid ester, thiolcarbamic acid ester, carbamic acid halide or urea;

b. by saponifying or hydrolyzing a corresponding X—CO—NH—A— substituted sulfonyl-isourea ether, sulfonyl-isothiourea ether, a sulfonyl-parabanic acid, a sulfonyl-haloformic acid amidine or a compound of the formula

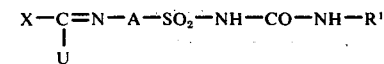

in which U represents low molecular O-alkyl, low molecular S-alkyl or halogen, preferably chlorine;

c. by replacing the thio-sulfur atom or the thio-sulfur atoms by oxygen in corresponding X—CO—NH—A— or X—CS—NH—A—substituted sulfonyl-thiourea or a X-CS-NH-A-substituted sulfonyl urea;

d. by adding water onto a corresponding X—CO—N-H—A-substituted sulfonyl-carbodiimide, e. by oxidizing a corresponding sulfinyl- or sulfenyl-urea;

f. introducing by acylation, optionally stepwise, the radical

X—CO— into a sulfonyl urea of the formula

or g. by reacting a X—CO—NH—A—substituted sulfonyl halide with a $R^1$-substituted urea or its alkali metal salt or a correspondingly substituted sulfinic acid halide or, in the presence of an acid condensation agent, a correspondingly substituted sulfinic acid or its alkali metal salts with a hydroxy-urea of the formula $R^1$—N-H—CO—NH—OH, and by treating the reaction product, if desired, with an alkaline agent for salt formation.

The mentioned sulfonyl-carbamic acid esters or sulfonyl-thiolcarbamic acid esters may contain an alkyl radical or an aryl radical in the alcohol component or even a heterocyclic radical. In view of the fact that this radical is separated during the reaction, its chemical nature has no importance on the character of the final product and can, therefore, be varied within wide limits. The same applies to the N—$R^1$-substituted carbamic acid esters or corresponding thiolcarbamic acid esters.

As carbamic acid halides, there are suitable in the first instance the chlorides.

The sulfonyl-ureas used as starting materials in the process of the invention may be unsubstituted or substituted once or, in particular twice, at the side opposite to the sulfonyl group. Since these substituents are split off during the reaction with amines, their character may be varied within wide limits. Besides alkyl-, aryl-, acyl- or heterocyclic substituted sulfonyl ureas, there may also be used sulfonyl-carbamoylimidazoles and similar compounds or bis-sulfonyl-ureas which may carry at one of the nitrogen atoms, for example methyl. It is possible, for example to treat such bis-sulfonyl ureas or also N-sulfonyl-N'-acyl-ureas with R'-substituted amines and to heat the salts obtained to elevated temperatures, in particular to temperatures above 100° C.

Furthermore, it is possible to start from $R^1$-substituted ureas or from such $R^1$-substituted ureas which are substituted once or, in particular, twice at the free nitrogen atom and to react them with X—CO—N-H—A-substituted sulfonamides. As such starting substances, there may be used N-cyclopentylmethyl-urea, the corresponding N'-acetyl-, N'-nitro-, N'-cyclopentylmethyl-, N',N'-diphenyl- (in which the two phenyl radicals may be substituted or bound directly or over a bridge member such as —CH₂—, —NH—, —O— or —S— with each other), N'-methyl-N'-phenyl-, N',N'-di-cyclopentyl-methyl ureas as well as cyclopentyl-methyl-carbamoyl-imidazoles, -pyrazoles or -triazoles, and such of the mentioned compounds which carry instead of the cyclopentylmethyl group another substituent within the range of the definition of $R^1$.

The hydrolysis of the sulfonyl-parabanic acids, sulfonyl-isourea ethers, sulfonyl-isothiourea ethers or sulfonyl-haloformic acid amidines mentioned as starting substances is suitably carried out in an alkaline medium. Isourea ethers can also be hydrolyzed successfully in an acid medium. The replacement of the sulfur atom in the urea grouping of correspondingly substituted sulfonyl-thioureas by an oxygen atom can be effected in known manner, for example with the aid of oxides or salts of heavy metals or by application of oxidizing agents such as hydrogen peroxide, sodium peroxide, nitrous acid or permanganates.

The thio-ureas may also be desulfurized by treatment with phosgene or phosphorus pentachloride. Chloroformic acid amidines or carbodiimides obtained as intermediate products can be converted into the sulfonyl ureas by suitable measures such as saponification or addition of water.

Carbodiimides onto which water is to be added according to method (d) may be obtained, for example according to known methods from thioureas.

The isothiourea ethers behave toward some oxidizing agents, for example towards hydrogen peroxide, in the same manner as the corresponding thioureas. Accordingly, they may likewise be used as starting compounds for an oxidative desulfuration.

With regard to reaction conditions, the modes of operation of the process of the invention may be varied within large limits and adapted to the respective circumstances. For example, the reactions may be carried out in the absence or in the presence of solvents, at room temperature or at an elevated temperature.

Depending on the character of the starting substances, it may be that one or the other of the described processes in some cases gives a desired individual sulfonyl urea only in a very poor yield or is not suitable for its synthesis. In such rare cases, an expert will have no difficulties to synthesize the desired product according to another of the described methods of operation.

The blood sugar lowering action of the described sulfonyl ureas was determined by administering them in the form of the sodium salts in doses of 10 mg/kg to normally fed rabbits and by determining the blood sugar level according to the known method devised by Hagedorn-Jensen or with an autoanalyzer over a prolonged period of time.

For example, the N-[4-(β-< 6-chloro-quinoline-8-carboxyamido>-ethyl)-benzenesulfonyl]-N'-cyclopentyl-methyl-urea, the N-[4-(β-<2-methoxy-5-methyl-benzamido>-ethyl)-benzenesulfonyl]-N'-cyclopentyl-methyl-urea and the N-[4-(β->3-chloro-benzamido>-ethyl)-benzenesulfonyl]-N'-cyclopentyl-methyl-urea, when administered in the above-indicated doses, provoke a lowering of the blood sugar level by 50% and more.

The described sulfonyl-ureas serve preferably for the manufacture of orally administrable preparations having hypoglycemic action in the treatment of diabetes mellitus and may be administeredas such or in the form of their salts or in the presence of substances which cause salt formation. For the salt formation, there may be used, for example alkaline agents such as alkali metal or alkaline earth metal hydroxides, -carbonates or -bicarbonates, As medicinal preparations, there are used preferably tablets which contain, in addition to the products of the invention, the usual excipients and auxiliary agents such as talc, starch, lactose, tragacanth or magnesium stearate.

A preparation which contains the described sulfonyl-ureas as active ingredients, for example a tablet or a powder, with or without additions, is suitably brought into a suitable dosage unit form. The dose selected is then a dose which is adapted to the efficacy of the sulfonyl-urea used and to the desired effect. Suitably, the dose per unit is about 0.5 to 100 mg, preferably 2 to 10 mg, but it is also possible to use higher or lower dosage units, which can be divided or multiplied before their application.

The sulfonyl-ureas of the invention may be used alone for the treatment of diabetes mellitus or in combination with other oral antidiabetics. As such, there may not only be used bloodsugar lowering sulfonyl ureas, but also compounds having a different chemical structure, for example bi-guanides, in particular the phenylethyl-biguanide or the dimethyl-dibiguanide.

The following Examples show some of the numerous process variants which can be used for the synthesis of the sulfonylureas of the present invention, but they are in no respect a limitation of the object of the invention.

EXAMPLE 1:

N[4-($\beta$-<2-methoxy-5-methyl-benzamido>-ethyl)-benzene-sulfonyl]-N'-cyclopentyl-methyl-urea 20.3 g of N-[4-($\beta$-<2-methoxy-5-methyl-benzamido>-ethyl)-benzensulfonyl]-carbamic acid methyl ester (melting point 169° – 171° C) were dissolved in 100 ml of dioxane. After addition of 4.95 g of cyclopentylmethylamine, the whole was heated for 1 hour to the boiling temperature, under reflux. The clear solution was poured in a very diluted (about 0.25 %) aqueous ammonia solution, filtered with the use of charcoal and the filtrate was acidified with dilute hydrochloric acid. The N-[4-($\beta$-<2-methoxy-5-methyl-benzamido>-ethyl)-benzenesulfonyl]-N'-cyclopentyl-methyl-urea obtained was filtered off with suction. After recrystallization from methanol, it was found to melt at 147° – 149° C.

In analogous manner, there was obtained from cyclopentylmethylamine and

N-[4-($\beta$-<2-methoxy-benzamido>-ethyl)-benzensulfonyl]-carbamic acid methyl ester (melting point 173° – 175° C)

the N-[4-($\beta$-<2-methoxy-benzamido>-ethyl)-benzenesulfonyl]-N'-cyclopentyl-methyl urea melting at 152° – 154° C (from methanol), N-[4-($\beta$-<2-methoxy-5-chloro-benzamido>-propyl)-benzenesulfonyl]-carbamic acid methyl ester (melting point 201° – 103° C), the N-[4-($\beta$-<5-chloro-2-methoxy-benzamido>-propyl)-benzenesulfonyl]-Nm'-cyclopentyl-methyl-urea melting at 180° – 182° C (from methanol), N-[4-($\beta$-<2-methoxy-5-chloro-benzamido>-ethyl)-benzene-sulfonyl]-carbamic acid methyl ester (melting point 189° – 191° C)

the N-[4-($\beta$-<2-methoxy-5-chloro-benzamido>-ethyl)-benzenesulfonyl]-N'-cyclopentyl-methyl-urea melting at 173° – 174° C (from methanol), N-[4-($\beta$-<3-methoxy-5-chlorothiophene-2-carboxamido>-ethyl)-benzenesulfonyl]-carbamic acid methyl ester (melting point 186° – 188° C), the N-[4-($\beta$-<3-methoxy-5-chlorothiophene-2-carboxamido>-ethyl)-benzenesulfonyl]-N'-cyclopentyl-methyl-urea melting at 130° – 132° C (from water/ethanol), N-[4-($\beta$-<6-chloro-quinoline-8-carboxamido>-ethyl)-benzenesulfonyl]-carbamic acid methyl ester (melting point 199° – 201° C), the N-[4-($\beta$-<6-chloro-quinoline-8-carboxamido>-ethyl)-benzenesulfonyl]-N'-cyclopentyl-methyl-urea melting at 205° – 207° C (from methanol/dimethylformamide), N-[4-($\beta$-<2-ethoxy-5-chloro-benzamido>-ethyl)-benzenesulfonyl]-carbamic acid methyl ester (melting point 203° – 205° C), the N-[4-($\beta$-<2-ethoxy-5-chloro-benzamido>-ethyl)-benzenesulfonyl]-N'-cyclopentyl-methyl-urea melting at 181° – 182° C (from water/methanol), N-[4-($\beta$-<3-chloro-benzamido>-ethyl)-benzenesulfonyl]-carbamic acid methyl ester (melting point 171° – 173° C), the N-[4-($\beta$-<3-chloro-benzamido>-ethyl)-benzenesulfonyl]-N'-cyclopentyl-methyl-urea melting at 169° – 171° C (from methanol).

In analogous manner, there were obtained from 3-methyl-cyclopentylmethylamine and N-[4-($\beta$-<2-methoxy-5-chloro-benzamido>-ethyl)-benzenesulfonyl]-carbamic acid methyl ester (melting point 189° – 191° C)

the N-[4-($\beta$-<2-methoxy-5-chloro-benzamido>-ethyl)-benzenesulfonyl]-N'-(3-methyl-cyclopentyl-methyl)-urea melting at 157.5° – 158.5° C (from methanol), N-[4-($\beta$-<3-methoxy-5-chlorothiophene-2-carboxamido>athyl)-benzenesulfonyl]-carbamic acid-methyl ester, (melting point 186°–188°), N-[4-($\beta$-<3-methoxy-5-chlorothiophene-2-carboxamido>-ethyl)-benzenesulfonyl]-N'-(3-methyl-cyclopentyl-methyl)-urea melting at 162° – 163° C (from water/methanol/dimethylformamide), N-[4-($\beta$-<6-chloro-quinoline-8-carboxamido>-ethyl)-benzenesulfonyl]-carbamic acid methyl ester (melting point 199° – 201° C), the N-[4-($\beta$-<6-chloro-quinoline-8-carboxamido>-ethyl)-benzenesulfonyl]-N'-(3-methyl-cyclopentyl-methyl)-urea melting at 162° – 163° C (from water/methanol/dimethylformamide).

In analogous manner, there were obtained from 2-ethyl-cyclopentylmethylamine and N-[4-($\beta$-<2-methoxy-5-fluoro-benzamido>-ethyl)-benzene-sulfonyl]-carbamic acid methyl ester (melting point 179° – 181° C), the N-[4-($\beta$-<2-methoxy-5-fluoro-benzamido>-ethyl)-benzenesulfonyl]-N'-(2-ethyl-cyclopentyl-methyl)-urea melting at 129° – 130° C (from methanol), N-[4-($\beta$-<2-methoxy-5-methyl-benzamido>-ethyl)-benzenesulfonyl]-carbamic acid methyl ester (melting point 175° – 177° C,)

the N-[4-($\beta$-<2-methoxy-5-methyl-benzamido>-ethyl)-benzenesulfonyl]-N'-(2-ethyl-cyclopentyl-methyl)-urea melting at 128° – 130° C (from methanol), N-[4-($\beta$-<2-ethoxy-5-chloro-benzamido>-ethyl)-benzenesulfonyl]-carbamic acid methyl ester (melting point 203° – 205° C), the N-[4-($\beta$-<2-ethoxy-5-chloro-benzamido>-ethyl)-benzenesulfonyl]-N'-(2-ethyl-cyclopentyl-methyl)-urea melting at 126° – 128° C (from methanol).

In analogous manner, there were obtained from cyclopentylethylamine and

N-]4-(β-<2-methoxy-5-methyl-benzamido>-ethyl)-benzenesulfonyl]-carbaamic acid methyl ester (melting point 169° – 171° C)

the N-[4-(β-<2-methoxy-5-methyl-benzamido>-ethyl)-benzenesulfonyl]-N'-cyclopentyl-ethyl-urea melting at 177.5° – 179.5° C (from methanol), N-[4-(β-<2-methoxy-5-chloro-benzamido>-ethyl)-benzene-sulfonyl]-carbamic acid methyl ester (melting point 189° – 191° C), the N-[4-(β-<2-methoxy-5-chloro-benzamido>-ethyl)-benzenesulfonyl]-N'-cyclopentyl-ethyl-urea melting at 149°–151.5° C (from methanol), N-[4-(β-<2-methoxy-benzamido>-ethyl)-benzenesulfonyl]-carbamic acid methyl ester (melting point 173° – 175° C), the N-[4-(β-<2-methoxy-benzamido>-ethyl)-benzenesulfonyl]-N'-cyclopentyl-ethyl-urea melting at 161° – 163° C (from methanol), N-[4-(β-<3-ethoxy-thiophene-2-carboxamido>-ethyl)-benzenesulonyl]-carbamic acid methyl ester (melting point 163° – 165° C), the N-[4-(β-<3-ethoxy-thiophene-carboxamido>-ethyl)-benzenesulfonyl]-N'-cyclopentyl-ethyl-urea melting at 177.5° – 179° C (from methanol), N-[4-(β-<2-methoxymethoxy-benzamido>-ethyl)-benzenesulfonyl]-carbamic acid methyl ester (melting point 157° – 159° C), the N-[4-(β-<2-methoxymethoxy-benzamido>-ethyl)-benzenesulfonyl]-N'-cyclopentyl-ethyl-urea melting at 115° – 117° C (from methanol), N-[4-(β-<3-chloro-benzamido>-ethyl)-benzenesulfonyl]carbamic acid methyl ester (melting point 171° – 173° C), the N-[4-(β-<3-chlorobenzamido>-ethyl)-benzenesulfonyl]-N'-cyclopentyl-ethyl-urea melting at 160° – 161° C (from methanol).

EXAMPLE 2

N-[2-(5-methyl-2-methoxybenzamido)-1,2,3,4-tetrahydronaphthalene-7-sulfonyl]-N'-cyclopentyl-methyl-urea 2 g of 2-(5-methyl-2-methoxybenzamido)-1,2,3,4-tetrahydronaphthalene-7-sulfonamide were dissolved in a solution of 1.2 g of sodium in 16 ml of methanol and the whole was evaporated to dryness. The residue was suspended in 40 ml of acetone, combined with 0.7 g of cyclopentylmethyl-isocyanate and then boiled for 4 hours. The whole was filtered with suction and the residue was dissolved in a solution of sodium bicarbonate. The solution was filtered over active charcoal and acidified with dilute hydrochloric acid. The sulfonyl-urea that had precipitated was found to sinter at 100° C and to have a melting point at 188° – 120° C.

EXAMPLE 3

N-[2-(5-chloro-2-methoxybenzamido)-indane-5-sulfonyl]-N'-cyclopentylmethyl-urea 2.4 g of N-(2-aminoindane-5-sulfonyl)-N'-cyclopentyl-methylurea (melting point 192° – 194° C, prepared by saponification of 2-N-(acetamido-indane-5-sulfonyl)-N'-cyclopentyl-methyl-urea, melting point 107° – 109° C) were dissolved in 10 ml of water and 3.6 ml of 2N-sodium hydroxide solution. Then, a solution of 1.7 g of 5-chloro-2-methoxy-benzoyl chloride in 6 ml of methylene chloride was added dropwise, while cooling, and the whole was stirred for 1 hour; the mixture was slowly heated and the methylene chloride was evaporated. The sulfonyl-urea that had precipitated was filtered off with suction and dissolved in dilute sodium hydroxide solution. The whole was then treated with active charcoal, filtered and the sodium salt was precipitated by the addition of concentrated sodium hydroxide solution. The sodium salt was dissolved in water and precipitated again by the addition of sodium hydroxide solution. Finally, the free compound was precipitated from the alkaline solution with hydrochloric acid and recrystallized from methanol. Melting point 194° – 196° C.

EXAMPLE 4

N-[4-(β-<2-methoxy-5-methyl-benzamido>-ethyl)-benzenesulfonyl]-N'-cyclopentyl-methyl-urea 14.5 g of N-[4-(β-<2-methoxy-5-methyl-benzamido>-ethyl)-benzenesulfonyl]-N'-phenyl-thiourea were dissolved in 50 ml of dioxane. After addition of 6 g of cyclopentyl-methylamine, the whole was heated for 2 hours to the boiling temperature under reflux. After having removed the dioxane by distillation, the residue was dissolved in 1% aqueous ammonia. The solution was filtered through charcoal and acidified with dilute hydrochloric acid. The N-[4-(β-<2-methoxy-5-methyl-benzamido>-ethyl)-benzenesulfonyl]-N'-cyclopentyl-methyl-thiourea so obtained was found to melt, after recrystallization from methanol, at 152° – 154° C.

4.89 g of N-[4-(β-<2-methoxy-5-methyl-benzamido>-ethyl)-benzenesulfonyl]-N'-cyclopentyl-methyl-thiourea were dissolved in 20 ml of 2N-sodium hydroxide solution and 10 ml of dioxane. After addition of 20 ml of 30% hydrogen peroxide, the whole was heated for 15 minutes on the steam bath. The mixture was acidified with 2N-hydrochloric acid and the crystals were filtered off. The N-[4-(β-<2-methoxy-5-methyl-benzamido>-ethyl)-benzenesulfonyl]-N'-cyclopentyl-methyl-urea was found to melt, after recrystallization from methanol, at 148° – 150° C.

The same compound was obtained by desulfurizing the N-[4-(β-<2-methoxy-5-methyl-benzamido>-ethyl)-benzenesulfonyl]-N'-cyclopentyl-methyl-thiourea by treatment with HgO in the presence of sodium hydroxide solution. For this purpose, 0.5 g of the thiourea were dissolved in 10 ml of dioxane and 10 ml of 2N-sodium hydroxide solution. 0.22 g of HgO was added and the whole was stirred for 5 hours at 40° C. The HgS that had formed was removed by filtration, the filtrate was acidified and the precipitate that had separated and constituted the N-[4-(β-<2-methoxy-5-methyl-benzamido>-ethyl)-benzenesulfonyl]-N'-cyclopentyl-methyl-urea was isolated. After recrystallization from methanol, the compound was found to melt at 148° – 150° C.

EXAMPLE 5

N-[4-(β-<3-methoxy-5-chlorothiophene-2-carboxamido>-ethyl)-benzenesulfonyl]-N'-(2-ethyl-cyclopentyl-methyl)-urea 4.33 g of N-[4-(β-<3-methoxy-5-chlorothiophene-2-carboxamido>-ethyl)-benzenesulfonyl]-carbamic acid methyl ester (melting point 186° – 188° C) were dissolved in 100 ml of dioxane and, after addition of 1.2 g of 2-ethyl-cyclopentylmethylamine, kept for 2 hours under reflux. The clear solution was poured into dilute aqueous ammonia solution, filtered and acidified with 2N-hydrochloric acid. The N-[4-(β-<3-methoxy-5-chlorothiophene-2-carboxamido>-ethyl)-benzenesulfonyl]-N'-(2-ethyl-cyclopentyl-methyl)-urea so obtained was found to melt at 160° – 161° C after recrystallization from methanol.

In analogous manner, there were obtained from 2-ethyl-cyclopentylmethylamine and N-[4-(β-<2-methoxy-5-chloro-benzamido>-ethyl)-benzenesulfonyl]-carbamic acid methyl ester (melting point 189° – 191° C), the N-[4-(β-<2-methoxy-5-chloro-benzamido>-ethyl)-benzenesulfonyl]-N'-(2ethyl-cyclopentyl-methyl)-urea melting at 129° – 130° C (from methanol), N-[4-(β-<2-methoxy-5-trifluoromethyl-benzamido>-ethyl)-benzenesulfonyl]-carbamic acid methyl ester (melting point 167° – 170° C), the N-[4-(β-<2-methoxy-5-trifluoromethyl-benzamido>-ethyl)-benzenesulfonyl]-N'-(2-ethyl-cyclopentyl-methyl)-urea melting at 129° – 130° C (from methanol).

In analogous manner, there was obtained from 3-methyl-cyclopentylmethylamine and N-[4-(β-<2-methoxy-5-bromo-benzamido>-ethyl)-benzenesulfonyl]-carbamic acid methyl ester (melting point 197° – - 199° C), the N-[4-(β-<2-methoxy-5-bromo-benzamido>-ethyl)-benzenesulfonyl]-N'-(3-methyl-cyclopentyl-methyl)-urea melting at 150° – 151° C (from methanol).

EXAMPLE 6:

N-[4-(β-<2-methoxy-5-methyl-benzamido>-ethyl)-benzenesulfonyl]-N'-cyclopentyl-methyl-urea 0.5 g of N[4-(β-<2-methoxy-5-methyl-benzamido>-ethyl)-benzenesulfonyl]-N'-cyclopentylmethyl-thiourea were dissolved in 50 ml of methanol. 0.22 g of HgO and a small amount of $K_2CO_3$ were added, while stirring, and the whole was heated for 3 hours, while continuing stirring, to 50° – 55° C. After having removed by filtration the HgS that had formed, the reaction mixture was concentrated whereupon the N-[4-(β-<2-methoxy-5-methylbenzamido>-ethyl)-benzenesulfonyl]-N'-cyclopentyl-methyl-isurea methyl-ether was obtained in the form of a viscous resin. A sample of the mentioned isourea ether was introduced into a test tube, concentrated hydrochloric acid was poured over it and the whole was heated on a steam bath for some minutes, while stirring with a glass rod. The crystalline product so obtained, constituting the N-[4-(β-<2-methoxy-5-methyl-benzamido>-ethyl)-benzenesulfonyl]-N'-cyclopentyl-methyl-urea was recrystallized from methanol. Melting point: 148° – 150° C.

EXAMPLE 7

N-[4-(β-<2-methoxy-5-methyl-benzamido>-ethyl)-benzensulfonyl]-N'-cyclopentyl-methyl-urea 2.44 g of N-[4-(β-<2-methoxy-5-methyl-benzamido>-ethyl)-benzenesulfonyl]-N'-cyclopentyl-methyl-thio-urea (I) were dissolved together with 1.03 g of dicyclohexylcarbodiimide in 20 ml of hot dioxane. The whole was allowed to cool and to stand for several days. Thereupon, the N,N'-dicyclohexyl-thiourea that had formed (melting point 176° – 178° C) was filtered off with suction. The filtrate which contained the N-[4-(β-<2-methoxy-5-methyl-benzamido>ethyl)-ben-zenesulfonyl]-N'-cyclopentyl-methyl-carbodiimide (II) in dissolved state, was combined with about 5 ml of water. The whole was shortly heated on a water bath and concentrated. The residue was dissolved in a mixture of toluene, ether and dilute aqueous ammonia, while shaking. The aqueous phase was separated. The toluene/ether phase was extracted again with dilute ammonia. The aqueous extracts were united and acidified. There was obtained a precipitate, constituting the N-[4-(β-<2-methoxy-5-methyl-benzamido>-ethyl)-benzenesulfonyl]-N'-cyclopentylmethylurea (III). After recrystallization from methanol, the sulfonylurea was found to melt at 148° – 150° C.

EXAMPLE 8

N-[4-(β-<2-methoxy-5-chlorobenzamido>-ethyl)-benzenesulfonyl]-N'-cyclopentylmethyl-urea 7.1 g of cyclopentylmethyl-urea were suspended in 100 ml of absolute benzene and combined with 2.4 g of 50% sodium hydride. The whole was heated for 3 hours at 50° C, 9.7 g of 4-(β-<2-methoxy-5-chlorobenzamido>-ethyl)-benzenesulfochloride in 100 ml of absolute benzene were added and the reaction mixture was stirred for 3 hours at 80° C. After cooling, the reaction mixture was extracted several times with water and, after filtration, the combined aqueous extracts were acidified with hydrochloric acid. The reaction product that had precipitated was dissolved and reprecipitated from 1% ammonia and recrystallized from methanol. The N-[4-(β-<2-methoxy-5-chlorobenzamido>-ethyl)-benzenesulfonyl]-N'-cyclopentylmethyl-urea so obtained was found to melt at 173° – 174° C.

EXAMPLE 9

N-[4-(β-<2-methoxy-5-chlorobenzamido>-ethyl)-benzenesulfonyl]-N'cyclopentylmethyl-urea 6,8 g of 4-(β-<2-methoxy-5-chlorobenzamido>-ethyl)-benzensulfinyl chloride (prepared from 4-(β-<2-methoxy-5-chloro-benzamido->-ethyl)-benzene-sulfinic acid and thionyl chloride) were introduced into a suspension of 2.8 g of cyclopentylmethyl-urea in 30 ml of pyridine. After 10 minutes, the mixture was poured into 100 ml of ice water to which 20 ml of 2N-hydrochloric acid had been added previously. The precipitate that had separated was treated with 1% ammonia, the residue was dissolved in dimethylformamide and the solution was combined, while stirring, with an aqueous solution of potassium permanganate until the permanganate colour remained constant. The solution was then discoloured with a small amount of bisulfite, the manganese dioxide was filtered off and the filtrate was combined with water and hydrochloric acid. The N-[4-(β-<2-methoxy-5-chlorobenzamido>-ethyl)-benzenesulfonyl]-N'-cyclopentylmethyl-urea was recrystallized from methanol and was found to melt at 173° – 174° C.

We claim:
1. A compound of the formula

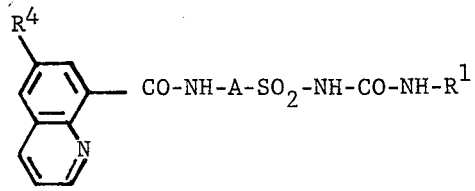

in which
R¹ represents cyclopentylmethyl, alkyl-cyclopentylmethyl or dialkyl-cyclopentylmethyl having up to 2 carbon atoms in the alkyl moiety or cyclopentylethyl,
R⁴ represents H, Cl or Br,
A represents
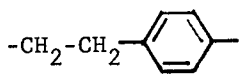 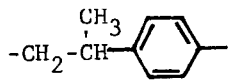 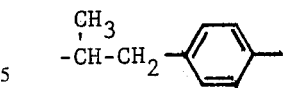 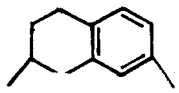
or
and physiologically tolerated salts thereof.
2. N-[4-(β-<6-chloro-quinoline-8-carboxamido>-ethyl)-benzenesulfonyl]-N'-cyclopentyl-methyl-urea.
* * * * *